US009345732B2

(12) United States Patent
Gokaraju et al.

(10) Patent No.: US 9,345,732 B2
(45) Date of Patent: May 24, 2016

(54) AGENTS DERIVED FROM HOLOPTELEA INTEGRIFOLIA AND THEIR COMPOSITIONS FOR THE CONTROL OF METABOLIC SYNDROME AND ASSOCIATED DISEASES

(75) Inventors: Ganga Raju Gokaraju, Andhra Pradesh (IN); Rama Raju Gokaraju, Andhra Pradesh (IN); Venkata Kanaka Ranga Raju Gokaraju, Andhra Pradesh (IN); Trimurtulu Golakoti, Andhra Pradesh (IN); Kiran Bhupathiraju, Andhra Pradesh (IN); Venkateswara Rao Chirravuri, Andhra Pradesh (IN); Sivaramakrishna Chillara, Andhra Pradesh (IN)

(73) Assignee: Laila Nutraceuticals, Andhra Pradesh (IN)

( * ) Notice: Subject to any disclaimer, the term of this patent is extended or adjusted under 35 U.S.C. 154(b) by 38 days.

(21) Appl. No.: 13/510,815

(22) PCT Filed: Nov. 19, 2009

(86) PCT No.: PCT/IN2009/000662
§ 371 (c)(1),
(2), (4) Date: May 18, 2012

(87) PCT Pub. No.: WO2011/061749
PCT Pub. Date: May 26, 2011

(65) Prior Publication Data
US 2012/0231095 A1 Sep. 13, 2012

(51) Int. Cl.
*A61K 36/185* (2006.01)
*A61K 36/67* (2006.01)
*A61K 36/16* (2006.01)
*A61K 36/58* (2006.01)
*A23L 1/30* (2006.01)

(52) U.S. Cl.
CPC ............. *A61K 36/185* (2013.01); *A23L 1/3002* (2013.01)

(58) Field of Classification Search
None
See application file for complete search history.

(56) References Cited

U.S. PATENT DOCUMENTS

| 5,607,691 | A | 3/1997 | Hale et al. |
| 6,149,915 | A | 11/2000 | Li et al. |
| 6,225,451 | B1 | 5/2001 | Ballinger et al. |
| 2005/0032761 | A1 | 2/2005 | Morton et al. |
| 2005/0233011 | A1 | 10/2005 | Beavers |
| 2006/0141068 | A1* | 6/2006 | Palpu et al. .................. 424/725 |
| 2006/0159784 | A1* | 7/2006 | Ghosal .......................... 424/762 |
| 2006/0286183 | A1* | 12/2006 | Gardiner et al. ............. 424/745 |
| 2007/0088088 | A1 | 4/2007 | Inada et al. |
| 2007/0237786 | A1* | 10/2007 | Heuer ....................... 424/195.17 |
| 2007/0248959 | A1 | 10/2007 | Ordovas et al. |
| 2008/0280376 | A1 | 11/2008 | Handberg |
| 2010/0203078 | A1* | 8/2010 | Gokaraju et al. ......... 424/195.18 |
| 2012/0301432 | A1* | 11/2012 | Gokaraju et al. ............ 424/93.1 |

FOREIGN PATENT DOCUMENTS

| IN | 200500744 | * | 3/2006 |
| KR | 2005003321 | A | 1/2005 |
| KR | 10661478 | | 12/2006 |
| KR | 20070070311 | | 7/2007 |
| WO | 2004045604 | | 6/2004 |
| WO | 2004045605 | | 6/2004 |
| WO | 2008086403 | | 7/2008 |
| WO | 2008093848 | | 8/2008 |
| WO | 2009/024991 | | 2/2009 |

OTHER PUBLICATIONS

Reddy et al. J. Ethnopharmacol. 2008. vol. 115, p. 249-256 (available online Oct. 13, 2007).*
Kumar P et al. Ethnobotanical Leaflets. Oct. 2009. vol. 13, pp. 1222-1231.*
Mariapackiam et al. J. Adv. Zool. 2007. Vo.. 28, No. 1, pp. 32-38.*
M. Rama Rao et al, International Seminar on Medicinal Plants & Herbal Products [ISMPHP] Apr. 22, 2008; Tirupathr, India. URL: http://ismphpabstracts.blogspot.com/ (viewed May 7, 2012).
Rajbhandari, M et al., Screening of Nepalese medicinal plants for antiviral activity, 2001; J Ethnopharmacol, 74: 251-255.
Kelishadi R, Childhood Overweight, Obesi and the Metabolic Syndrom in Developing Countries, Epidemiol Rev, 2007; 29: 62-76.
Scott M. G., et. al., Definition of Metabolic Syndrome: Report of the National Heart, Lung, and Blood Institute/American Heart Association Conference on Scientific Issues Related to Definition, Circulation 2004; 109; 433-438.
Wilson P W F, et. al, Prediction of Coronary Heart Disease Using Risk Factor Categories, Circulation 1998; 97: 1837-1847.
Gerard, T. C., et. al, Revisiting the metabolic syndrome, MJA 2006; 185: 445-449.
Jayaprakasam et al., Potent lipid peroxication inhibitors from Withania somifera fruits, Tetrahedrom, 2004, vol. 60, No. 13, pp. 3109-3121.
Sztalryd et al., Functional Compensation for Adipose Differentiation-related Protein by Tip47 in an ADFP Null Embryonic Cell Line Journal of Bilogical Chemistry, 2006, vol. 81, No. 45.

(Continued)

*Primary Examiner* — Chris R Tate
(74) *Attorney, Agent, or Firm* — Kramer & Amado, P.C.

(57) ABSTRACT

The invention discloses phytochemical agents derived from *Holoptelea integrifolia* and novel composition(s) comprising at least one component selected from the extract(s), fraction(s) and active compound(s) for the protection and alleviation of Metabolic Syndrome, insulin resistance, endothelial dysfunction, chronic kidney disease, atherosclerosis, diabetes and other disease conditions associated with metabolic syndrome. The invention also discloses the amelioration of certain biomarker molecules such as Peroxisome proliferator-activated receptor gamma (PPAR-γ), Adipose Differentiation Related Protein (ADRP), CD36, Adipocyte Fatty-acid-Binding Protein (aP2/FABP-4/A-FABP), beta-3 Adrenergic Receptor (β3AR), Leptin, Perilipin and Adiponectin by using the phytochemical components derived from *Holoptelea integrifolia*.

19 Claims, 9 Drawing Sheets

(56) References Cited

OTHER PUBLICATIONS

International Search Report dated Nov. 4, 2010 for PCT/IN2009/000662.

Kuboyama, et al., "Neuritic regeneration and synaptic reconstruction induced by withanolide A", British Journal of Pharmacology, 144, 961-971 (2005).

Bhārata Bhaiṣajya Ratnākara—Compiled by Nagīnadāsa Chaganalāla Śāha, Translated by Gopinath Gupta—vol.-I, 06 (p. 04-09) (p. of publication:27 ), Edn. 2nd. Reprint, Aug. 1999, B. Jain Publishers, New Delhi, India.†

Bhārata Bhaiṣajya Ratnākara Compiled by Nagīnadāsa Chaganalāla Śāha, Translated by Gopinath Gupta—vol.-V, 08 (p. 10-17) (p. of publication: 247), Aug. 1999, B. Jain Publishers, New Delhi, India.†

Suśruta, Suśruta Saṁhitā—Edited & translated by P.V Sharma vol.-II, 07 (p. 18-24) (p. of publication: 376), Edn. 1st, 2000, Chaukhamba Visvabharati, Varanasi, India.†

\* cited by examiner
† cited by third party

AGENTS DERIVED FROM HOLOPTELEA INTEGRIFOLIA AND THEIR COMPOSITIONS FOR THE CONTROL OF METABOLIC SYNDROME AND ASSOCIATED DISEASES

FIELD OF INVENTION

The present invention relates to pharmaceutical, nutraceutical and dietary supplement agents derived from *Holoptelea integrifolia* and their compositions for alleviating metabolic syndrome, diabetes and atherosclerosis and other disease conditions associated with metabolic syndrome.

The invention further includes amelioration of biomarker proteins or molecules, whose expression/production is altered during the metabolic syndrome and disease conditions associated with metabolic syndrome, by the phytochemical agents derived from *Holoptelea integrifolia* and their compositions.

BACKGROUND OF THE INVENTION

*Holoptelea integrifolia/Ulmus integrifolia* belongs to the family Ulmaceae. It is commonly known as Indian Elm Tree. The plant grows in India in the regions of Gujarat, Madhya Pradesh, Haridwar and in the Himalayas. Fruit is a samara (winged) nearly orbicular, 2 cms in diameter, on a slender stalk, wings membranous, tip bifid and lobes incurved. Fruits are plucked off the felled branches, cleaned and dried in the sun.

It is known by many local names, but more popularly as Kanju, Papri, Nemali etc. The seed oil is a good source of edible oil. Its leaves are commonly used along with a blend of other Ayurvedic herbs in herbal tea preparations for detoxification and rejuvenation. This herbal tea is also known to clear cellulite deposits and obliterates stretch marks that are fallen out of a weight problem. *Holoptelea integrifolia* was shown to exhibit antiviral activity in vitro assays and was recognized as one of the plant species useful to control air pollution.

*Holoptelea integrifolia* chemistry includes Steroids and triterpenoids; Triterpenoid constituents like amyrin, friedelin, epifriedelinol, friedel-1-en-3-one, lupeol, sitosterol, sitosterol-D-glucoside and stigmasterol in the petroleum ether extracts of the seeds; 2-alpha, 3-alpha-dihydroxyolean-12-en-28-oic acid isolated from the heartwood; two new triterpenoid fatty acid esters viz., Holoptelin A & B were also isolated.

Some of the non-patent literature of *Holoptelea integrifolia* is quoted below:

In India *Holoptelea integrifolia* has several medicinal properties and is used in conditions like rheumatism, to treat intestinal tumors, as an oxytocic in pregnant ladies, to treat common fevers. A combination of *Holoptelea* leaves with garlic and pepper is useful for treating Jaundice and the Stem bark acts as an anti-inflammatory agent specifically for eyes.

The methanol extract of bark exhibited significant radical scavenging activities and 5-Lipoxygenase inhibition activities. [M. Rama Rao et al, International Seminar on Medicinal Plants & Herbal Products [ISMPHP] Apr. 22, 2008; Tirupathi, India. URL: http://ismphpabstracts.blogspot.com/].

Bark and leaf paste are applied externally on the white patches of the skin. Leaves along with garlic are externally used to treat ringworm, eczema and cutaneous diseases. In Nepal, bark is externally used to relieve rheumatic swellings [Rajbhandari, M et al., 2001; *J Ethnopharmacol*, 74: 251-255].

The inventors have reported the antiobesity activity of *Holoptelea integrifolia* ameliorated through the inhibition of adipogenesis in the earlier PCT application (# PCT/IN2007/000356, filed Aug. 20, 2007). The effects of *Holoptelea integrifolia* on metabolic syndrome, atherosclerosis and diabetes have not been reported. The present invention thus involves a more significant and much effective metabolic marker amelioration shown by agents derived from *Holoptelea integrifolia* and their compositions for alleviating metabolic syndrome and other related diseases especially endothelial dysfunction, chronic kidney disease, atherosclerosis and diabetes.

Some of the patents related to the genus *Ulmus* and family Ulmaceae are quoted below:

Korean Patent KR20070070311 A relates to a composition for the prevention and treatment of Obesity and Hypercholesterolemia comprising extracts of natural products to reduce the number and size of adipocytes in the tissue, inhibit expression of genes associated with lipid synthesis including SREBP-1 (Sterol Response Element Binding Protein-1), FAS (Fatty Acid Synthase) and SCD-1 (Stearoyl CoA Desaturase) mRNA (messenger RNA) comprising the extracts of *Semisulcospira libertine*, sulfur fed duck, *Ulmus macrocarpa* Hance, pine pollen powder, *Acer tegmentosum* Maxim, bamboo salt, *Artemesia capillaries, Platycodon Grandiflorum* and Black bean in certain weight ratio.

Korean Patent KR10661478B1 relates to glycoprotein isolated from *Ulmus davidiana* nakai, and hepatoprotective and hypocholesterolemic pharmaceutical composition containing the glycoprotein.

U.S. Patent Publication US20060135444A1 and PCT Publications WO04045604A1, and WO04045605A1 relate to a nutritional composition suitable for reducing appetite, a method for the treatment and/or prevention of overweight and a method for the reduction of a mammalian appetite. The weight reduction and/or appetite reduction is achieved by administration of procyanidin and a flavonoid selected from the group consisting of chrysin, flavone, precursors of these flavonoids that are convertible into one of these flavonoids by gastrointestinal hydrolytic cleavage and mixtures thereof. In these publications the plant material or extract of plants like *Pinus aristata, Prunus domestica, Ulmus sieboldiana* etc., is used as a source of Flavonoid, preferably Chrysin.

Korean Patent KR2005003321A provides a method for manufacturing *Ulmus davidiana* juice which is used for treating inflammation, parasites, hypertension, cancer, diabetes and the like.

There is no prior art relating to the usage of *Holoptelea integrifolia* or its compositions for treating Metabolic Syndrome or for ameliorating metabolic marker proteins.

Metabolic Syndrome also known as Syndrome X/insulin resistance syndrome/Dysmetabolic Syndrome is a condition where in a group of diseased states which increase Atherosclerosis, Stroke and Diabetes. Metabolic Syndrome was first described as a cluster of interrelated common clinical disorders, including obesity, insulin resistance, glucose intolerance, hypertension and dyslipidemia.

A criteria for diagnosing Metabolic Syndrome was established by "The Adult Treatment Panel-III" (ATP-III) of the National Cholesterol Education Program in 2001. Five Criteria were selected by this Panel to identify individuals with Metabolic Syndrome including abdominal obesity, impaired fasting glucose, high triglyceride (TG), low HDL cholesterol (HDL-C) concentrations and increased blood pressure. Metabolic Syndrome is diagnosed, if any three of the components are present in an individual.

The definition set forth by the World Health Organization (WHO) includes diabetes or impaired glucose tolerance (IGT) and also lists thresholds for the risk factors of insulin resistance, raised arterial pressure, raised plasma triglycerides, central obesity, and microalbuminuria [Kelishadi R, *Epidemiol Rev.* 2007; 29: 62-76].

Obesity contributes to hypertension, high serum cholesterol, low HDL cholesterol, and hyperglycemia, and it otherwise associates with higher CVD risk. Abdominal obesity especially correlates with metabolic risk factors. Excess adipose tissue releases several metabolites that apparently exacerbate above risk factors. They include non-esterified fatty acids (NEFA), cytokines, PAI-1, and adiponectin [Scott M. G., et. al., *Circulation* 2004; 109; 433-438].

Hyper triglyceridemia and high density lipoprotein cholesterol (HDL-C), are two closely associated biochemical parameters that are commonly considered as syndrome criteria. Total cholesterol and low-density lipoprotein cholesterol (LDL-C) are considered to be significant risk factors for cardiovascular disease [Wilson P W F, et. al, *Circulation* 1998; 97: 1837-1847].

People with Metabolic Syndrome are at high risk of coronary heart disease, other diseases related to plaque buildups in artery walls (e.g., stroke and peripheral vascular disease) and type-2 diabetes.

The Metabolic Syndrome and most of its components were known to associate with a higher prevalence of calcified atherosclerotic plaque in the coronary arteries and abdominal aorta in white and African-American men and women.

Metabolic Syndrome has become a common affliction, affecting a quarter to a third of all adults, and its prevalence is rising, in parallel with increasing obesity and increasing aged population [Gerard, T. C., et. al, MJA 2006; 185: 445-449]. Hence, there is a need for the development of medicinal interventions for effective prevention, treatment and control of metabolic syndrome and diseased condition(s) associated with metabolic syndrome, especially those based on naturally agents or composition, as they believed to have minimum or negligible side effects.

A few prior art patents are quoted below which refer to the treatment and curing of Metabolic Syndrome.

PCT Publication WO08086403A1 describes the identification and isolation of chromones and novel chromone compositions from plant sources that are effective in enhancing adiponectin production by adipocytes and regulating genes involved in fatty acid biosynthesis. The invention also include methods for the prevention and treatment of a variety of diseases and conditions including, but not limited to insulin resistance, glucose intolerance, hyperglycemia, Metabolic Syndromes, dyslipidemia, and hypertriglyceridemia.

PCT Publication WO08093848A1 discloses a pharmaceutical product containing phosphatidylcholine derived from soybean for oral administration or for oral cavity application, a functional food and an oral composition which can prevent or ameliorate a disorder in the physical function induced by the increase in an inflammation marker, which can reduce the occurrence of Metabolic Syndrome or the risk of a disease and Metabolic Syndrome, and which can maintain or promote the healthy state.

As there is an urgent need for development of remedy for Metabolic Syndrome and the associated diseases, an effort was made by the inventors for finding a natural agent and composition which can be used for the effective control of Metabolic Syndrome in a safe manner and has minimized or has no side effects when compared to synthetic drugs available in the market.

SUMMARY OF THE INVENTION

In a primary aspect, the invention discloses agents derived from *Holoptelea integrifolia* which include extract(s), fraction(s), pure compound(s) or mixtures thereof and their compositions for the alleviation of Metabolic Syndrome, insulin resistance, endothelial dysfunction, chronic kidney disease, atherosclerosis, diabetes and other disease conditions associated with metabolic syndrome.

In another aspect, the invention discloses the amelioration of the expression/production of metabolic biomarker molecules related to metabolic syndrome, obesity, diabetes and atherosclerosis, endothelial dysfunction and chronic kidney disease, which include but not limited to Peroxisome proliferator-activated receptor gamma (PPAR-$\gamma$), Adipose Differentiation Related Protein (ADRP), CD36, Adipocyte Fatty-acid-Binding Protein (aP2/FABP-4/A-FABP), beta-3 Adrenergic Receptor ($\beta$3AR), Leptin, Perilipin and Adiponectin by the extract(s), active fraction(s), purified compound(s) of *Holoptelea integrifolia* and their compositions.

In another aspect, the invention provides that the agents derived from the plant parts selected from fruits, leaves, flowers, stem, bark, root or mixtures thereof of *Holoptelea integrifolia* can be used alone or optionally combined with nutraceutically or pharmaceutically or dietically acceptable vehicle(s) or carrier(s) including but not limited to distilled water, saline, aqueous glucose solution, alcohol (e.g. ethanol), propylene glycol and polyethylene glycol; and oily carriers such as various animal and vegetable oils, white soft paraffin, paraffin and wax or mixtures thereof.

Yet in another aspect, the invention provides that the agents of *Holoptelea integrifolia* and their compositions can be optionally combined with additional pharmaceutical, nutraceutical and dietary supplement agents, which include but not limited to antidiabetic agent(s), antihyperglycemic agent(s), hypolipidemic agent(s), antiobesity agent(s), antihypertensive agent(s), antiplatelet agent(s), antiinfective agent(s), anti-atherosclerotic agent(s) and anti-inflammatory agent(s).

In a further aspect, the invention provides the agents derived from *Holoptelea integrifolia* or their compositions for alleviating disease conditions selected from metabolic syndrome, diabetes, insulin resistance, increased insulin sensitivity, hyperinsulinemia, dyslipidemia, hypertriglyceridemia, chylomicronemia, low HDL-cholesterol, lipoprotein aberrations, decreased triglycerides, elevated uric acid levels, fatty liver, non-alcoholic fatty liver disease, polycystic ovarian syndrome, hemochromatosis (iron overload), acanthosis nigricans (dark patches on the skin), Impaired glucose tolerance (IGT), impaired fasting glucose (IFG), Type 2 diabetes, hypertension, atherosclerosis, endothelial dysfunction and cardio vascular diseases in mammals.

In another aspect, the invention also includes methods for the prevention and treatment of Metabolic Syndrome, atherosclerosis, diabetes, endothelial dysfunction, chronic kidney disease especially, the diseases and conditions mediated by insulin resistance in mammals. The method comprises of administering to a subject in need thereof an effective amount of agents comprising the extract(s) or active fraction(s) or active compound(s) or mixtures thereof derived from *Holoptelea integrifolia* and their compositions.

DETAILED DESCRIPTION OF THE INVENTION

Figure 1:
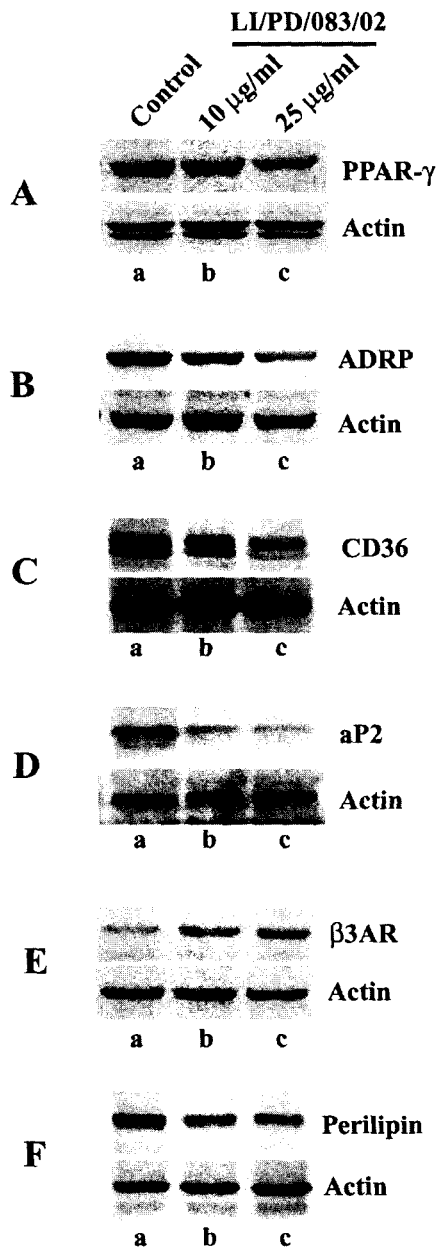
FIG. 1: Illustrates *Holoptelea integrifolia* leaf 60% methanol extract (LI/PD/083/02) modulating the metabolic marker proteins in 3T3-L1 adipocytes in a dose dependent manner. Representative immunoblots indicate down-regulation or upregulation of various marker proteins such as PPAR-γ (A), ADRP (B), CD36 (C), aP2 (D), β3AR (E) and Perilipin (F). Expression of actin protein was evaluated in each blot as the internal control. Expression of each protein was measured densitometrically and normalized with actin expression. The comparative levels are represented as bar diagrams (side panels). The bars a, b and c represent expression of various marker proteins in 3T3-L1 adipocytes treated with control, 10 μg/mL and 25 μg/mL of LI/PD/083/02 respectively.
Figure 1:
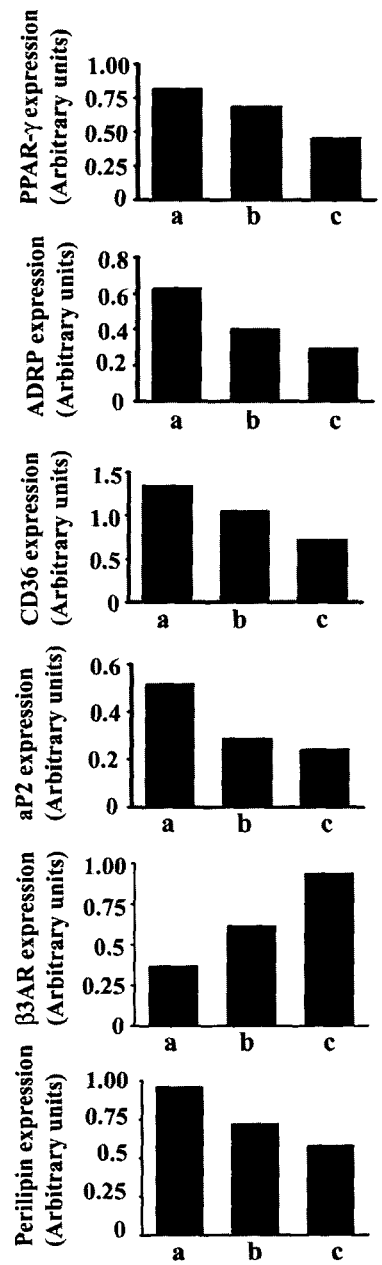

Metabolic syndrome is a condition involving a set of disorders that enhances the risk of heart disease. The major components of metabolic syndrome are excess weight, the cardiovascular parameters (high blood pressure, dyslipidemia, high levels of triglycerides and low levels of HDL in the blood) and insulin resistance. A subject suffering with several of these components, i.e., metabolic syndrome is greatly prone to heart disease, though each component is a risk factor.

Adipocytes and macrophages play important roles in the pathogenesis of metabolic syndrome and components associated with it. They both share a number of common features, including the ability to phagocytize and kill microorganisms and to secrete cytokines such as tumor necrosis factor α (TNF α) and interleukin-1 (IL-1). Critical transcription factors in adipocytes involved in regulating the expression of cytokines, inflammatory molecules, and fatty acid transporters are also expressed and have similar biologic roles in macrophages. For example, activation of PPAR-γ, a member of the nuclear-receptor super-family of ligand-activated transcription factors, is associated with differentiation of both types of cells. In adipocytes, PPAR-γ regulates adipocyte development and glucose homeostasis. In macrophages, PPAR-γ regulates expression of inflammatory genes and is involved in the development of atherosclerotic lesions.

Similarly, the adipocytes (fat cells) do not merely accumulate fat during the obesity development but also produce and circulate several low molecular weight bioactive protein molecules having powerful effects throughout the body. These markers are related to different components of metabolic syndrome. The expression and production of several of these metabolic markers, which include but not limited to Peroxisome proliferator-activated receptor gamma (PPAR-γ), Adipose Differentiation Related Protein (ADRP), CD36, Fatty-acid-Binding Protein (aP2/FABP-4/A-FABP), beta-3 Adrenergic Receptor (β3AR), adiponectin and Perilipin, become abnormal during the metabolic disease condition.

Atherosclerosis, also known as coronary heart disease (CHD), is one of the major vascular complication and important component of metabolic syndrome, which has enormous impact on the human health. It is a chronic inflammatory reaction to modified lipoproteins, primarily oxidized low density lipoproteins (Ox-LDL). Atherosclerosis is thought to develop as a result of lipid uptake by vascular-wall macrophages leading to the development of foam cells and the elaboration of cytokines and chemokines resulting in smooth muscle-cell proliferation (Berliner, J. A., *Circulation,* 91: 2488-2496, 1995, Boring, L., et. al., *Nature,* 394: 894-897, 1998). Cluster of Differentiation 36 (CD36) protein play a key role in the process of atherosclerosis.

The expression and production of the following protein markers related to different components of Metabolic Syndrome becomes abnormal during the disease condition. A brief description of the biomarker molecules that can be ameliorated and the mechanisms controlled by the present inventive agents derived from *Holoptelea integrifolia* and their compositions and their importance in control of Metabolic Syndrome and the conditions associated is given below:

1) Peroxisome Proliferator-Activated Receptor-γ (PPAR-γ):

PPAR-γ is a nuclear receptor that plays a pivotal role in obesity and diabetes. PPAR-γ has two isoforms, PPAR-γ1 and PPAR-γ2. An increase in adipose tissue mass can be the result of the production of new fat cells through the process of adipogenesis and the deposition of increased amounts of cytoplasmic triglyceride or lipid droplets per cell. In the adipogenesis process, proliferation of preadipocytes or precursor fat cells is followed by the differentiation of these cells to the mature adipocyte phenotype. PPAR-γ is expressed predominantly in adipose tissue, where it is known to play a critical role in adipocyte differentiation and fat deposition.

The activation of PPAR-γ on the other hand leads to an improvement of insulin action. PPAR-γ is the molecular target of the thiazolidinedione (TZD) class of antidiabetic drugs, such as troglitazone (Rezulin), rosiglitazone (Avandia), and pioglitazone (Actos). Adipose tissue development and insulin sensitivity are greatly impaired in PPAR-γ2 knockout mice indicating its role in obesity and diabetes. PPAR-γ is thus a key regulator of adipose cell differentiation, fatty acid uptake, and lipogenesis through its influence on the production of the enzymes required for lipid storage and metabolism [Zhang, J, *Proceedings of National Academy Sciences* 2004; 101; 10703-10708, 2004].

2) Adipose Differentiation Related Protein (ADRP):

ADRP is a 50 kDa protein and its mRNA (ADRP mRNA), which is 1.7 Kb in size, is expressed at high levels in adipose tissue. The expression of ADRP is very low in undifferentiated adipocytes, but ADRP mRNA reaches 50 to 100-fold a few hours after the onset of adipose differentiation process. ADRP is also found in many different types of cells and tissues, which accumulate or synthesize lipids. The foregoing thus indicates the possible role of ADRP in the formation or stabilization of lipid droplets in adipocytes and other cells. ADRP specifically enhances uptake of long chain fatty acids by adipose tissue. Hence ADRP is an important molecular target to identify the compounds that has the potential to control the obesity and diabetes through regulation of the expression of ADRP.

3) Adipocyte Fatty Acid Binding Proteins (FABP/aP2/FABP-4/A-FABP):

FABPs are molecular chaperones linked to metabolic and inflammatory pathways. Different members of the FABP family exhibit unique patterns of tissue expression/distribution and are expressed most abundantly in tissues involved in active lipid metabolism. FABPs play numerous functions. As lipid chaperones, for example, FABPs may actively facilitate the transport of lipids to specific compartments in the cell, such as to the lipid droplet for storage; to the endoplasmic reticulum for signaling, trafficking and membrane synthesis; to the mitochondria or peroxisome for oxidation [Masato, F et al, Nature Reviews/Drug Discovery, Vol. 7: 489-503, 2008]. A-FABP is Fatty Acid Binding Protein prominently expressed in mature adipocytes and macrophages. It is more familiarly known as FABP-4 and aP2. Adipocytes, however, express significantly higher levels (approximately 10000-fold) of A-FABP than macrophages, upon their differentiation from pre-adipocytes and monocytes respectively. A-FABP is abundantly present in human serum and it may play a central role in the development of major components of the metabolic syndrome such as obesity, type 2 diabetes and cardiovascular diseases, through its distinct actions in adipocytes and macrophages and its ability to integrate metabolic and inflammatory responses [Masato, F et al, Nature Reviews/Drug Discovery, Vol. 7: 489-503, 2008]. The aP2 expressed in adipocytes regulates systemic glucose and lipid metabolism. Blocking aP2 function is a novel approach to therapeutic strategy for the treatment of obesity, tracking heart disease, Metabolic Syndrome and other components of Metabolic Syndrome.

4) β3-Adrenergic Receptor (β3AR):

The body's adrenergic system plays a major part in regulating energy expenditure and lipolysis. In this process catecholamines mobilize energy-rich lipids by stimulating lipolysis in fat cells and thermogenesis in brown adipose tissue and skeletal muscle. Thus, β3AR is the principal receptor mediating catecholamine-stimulated thermogenesis in brown adipose tissue, which in humans is distributed about the great vessels in the thorax and abdomen [Thomas, G N, *International Journal of Obesity*, 545-551, 24, 2000]. The β3AR is also important in mediating the stimulation of lipolysis by catecholamines in the white fat cells of several species, including humans. The brown adipose tissue differs from white adipose tissue in that it has large numbers of mitochondria containing a so-called uncoupling protein, which can stimulate oxidative phosphorylation and thereby increase the metabolic rate. The role of brown adipose tissue is to oxidize lipids to produce heat and rid the body of excess fat. White adipose tissue, which includes subcutaneous and visceral adipose tissue, is much more abundant. It serves to store fat, which can be mobilized by lipolysis to generate free fatty acids for use by other tissues.

Selective agonists of β3ARs are potentially useful in treating obesity because they could enhance energy expenditure with few $β_1$- or $β_2$-adrenergic side effects. A number of β3-adrenergic agonists have been developed and tested experimentally. Hence the treatment with β3-selective agonists can markedly increase energy expenditure and decreases obesity.

5) Perilipin (PLIN):

PLIN is a protein that coats lipid droplets in adipocytes, the fat-storing cells in adipose tissue. Perilipin acts as a protective coating against body's natural lipases, such as hormone-sensitive lipase, that break triglycerides into glycerol and free fatty acids for use in metabolism through a process called lipolysis.

A study suggested that the family of Perilipin, adipophilin and TIP47 proteins may play key roles in obesity. PLIN is a candidate gene for obesity risk in humans as well as a modulator of dietary response to therapies aimed to reduce body weight and decrease Metabolic Syndrome risk. [Tai E S et al, *Curr Opin Lipidol.* 2007; 18(2):152-6].

Following β-adrenergic receptor activation, protein kinase A (PKA) hyperphosphorylates Perilipin localized at the surface of the lipid droplet. Phosphorylated perilipin changes conformation and translocate away from the lipid droplet, exposing the stored lipids to hormone-sensitive lipase-mediated hydrolysis of adipocyte triglycerides (lipolysis) to release nonesterified fatty acids (NEFA). Perilipin is thus an important regulator of lipid storage, lipolysis and energy balance. Perilipin expression is elevated in obese animals and humans. Studies manifested a significant positive relationship between perilipin expression and obesity (P<0.01, perilipin mRNA vs. percent body fat). Because of the potential importance of adipocyte lipolysis to obesity and insulin resistance, perilipin is an important target for developing anti-obesity drugs. Agents that inactivate perilipin may prove useful as anti-obesity medications.

6) Cluster of Differentiation 36 (CD36):

CD36 is a common molecule expressed by both adipocytes and macrophages. The CD36 expressed in adipocytes is known to function as a fatty acid transporter (FAT). Studies on adipocytes showed that CD36 mRNA is a marker of adipocyte differentiation. It is a scavenger receptor that binds and internalizes oxidized LDL (Ox-LDL) in macrophages. CD36 also functions as an LCFA transporter to facilitate the uptake of LCFAs in adipocytes. CD36 expression is up-regulated by PPAR-γ during the differentiation of both types of cells. It is also shown that the adipocytes can endocytose and lysosomally degrade Ox-LDL, mainly mediated by CD36. CD36 null animals showed significant decrease in binding and uptake of oxidized low density lipoprotein and showed significant increase in fasting levels of cholesterol, nonesterified free fatty acids, and triacylglycerol.

CD36 is a prototypic member of the class B scavenger receptor family. The endogenous (e.g., macrophages, adipocytes, platelets, microvascular endothelial cells and specialized epithelial cells) and ectopic (e.g., melanoma cells and fibroblasts) expression of this multi-ligand receptor on the surface of cells confers phagocytic activity for engulfment of apoptotic cells. CD36 is widely expressed and may interact with multiple extracellular ligands including thrombospondin-1 (TSP-1), long chain free fatty acids (FFAs), modified (oxidized) low-density lipoprotein (Ox-LDL), advanced glycation end (AGE) products, collagen I and collagen IV [PLoS Medicine, 2: 152-161, 2005]. CD36 is expressed on the surface of monocytes and macrophages and mediates uptake of oxidized low-density lipoprotein (Ox-LDL) [Nozaki, S., *J. Clin. Invest.* 96: 1859-1865, 1995] as well as to play a role in diverse cellular processes including foam cell formation, fatty acid transport, engulfment and removal of senescent cells, suppression of angiogenesis, and cell-matrix interactions. CD36-dependent uptake of Ox-LDL has been shown to be critical to cholesterol accumulation and subsequent foam cell formation; activities that likely contribute to the observed involvement of CD36 in mouse models of atherogenesis [Michael E et al, J. Exp. Med., 203: 2613-25, 2006].

CD36 may initiate atherosclerotic lesions and can be an important risk factor of cardiovascular disease. In mice lacking the CD36 receptor, foam-cell formation and vascular lesion development were indeed interrupted [Febbraio M., et. al., *J Clin Invest* 105:1049-1056, 2000]. Hyperglycemia-induced synthesis of CD36 in macrophages has been associated with increased uptake of Ox-LDL by macrophages and foam cell formation in atherosclerotic lesions in people with diabetes (PLoS Medicine, 2: 152-161, 2005]. The foregoing data thus demonstrate a correlation between increased CD36 expression and hyperglycemia in atherosclerotic vascular lesions, which thus offers potential opportunity and advantage to use CD36 as a potential molecular maker of atherosclerosis.

7) Leptin:

Leptin plays an important role in regulating energy expenditure in response to food intake. Leptin levels are doubled in the CD36-null mouse. Targeting adipocyte CD36 may offer a way to uncouple leptin production and adiposity. [Hajri T et al., *Diabetes.* 2007; 56(7): 1872-80].

Leptin is an important adipocytokine of adipose tissues, which further contain low and medium molecular weight proteins like adiponectin, tumor necrosis factor-alpha (TNF-alpha), interleukin-6 (IL-6), resistin, plasminogen-activating inhibitor-I (PAI-1), and angiotensinogen. Together these cytokines play an important role in the adipose tissue physiology and are believed to be a link between obesity, insulin resistance and endothelial dysfunction.

8) Adiponectin:

Adiponectin is an important adipokine and it was proved that low levels of adiponectin are associated with disease states such as obesity, diabetes and cardiovascular disease. Administration of adiponectin was proved to be beneficial in animal models of diabetes, obesity and atherosclerosis.

Adiponectin level in blood is decreased in obesity and it is considered to have antidiabetic and antiatherogenic effect. Whereas increased leptin level in blood in obesity is associated with regulation of appetite, energy expenditure, lipids and carbohydrates metabolism, cellular differentiation. In a study carried out on 80 patients (43 female and 37 male) from Obese families, the fasting level of leptin (Elisa), adiponectin (Elisa) and von Willebrand factor (Elisa) lipidogram were evaluated. It was found that the leptin to adiponectin ratio (Lep/AdipoR) in the blood was significantly higher in obese patients in comparison to people with normal BMI.

It was also proved that high plasma concentrations of adiponectin are associated with lower risk of Myocardial Infarction in men. [Pischon T et al., *JAMA.* 2004 April 14; 291(14): 1730-7]. Hence the phytochemical extracts or fractions or compounds that enhance the adiponectin levels can have beneficial effects on metabolic syndrome and disease components associated with metabolic syndrome.

Metabolic Syndrome is recognized as an important disease which can be single or can be a set of diseased conditions and if left untreated leads to several complications. Even though several classes of drugs are available in the market for the treatment of the major components of Metabolic Syndrome such as obesity, diabetes and atherosclerosis, many of them are associated with a number of side effects. Very few medicines are available to treat Metabolic Syndrome and none of them are comprehensive in addressing all the associated diseases. Hence there exists a great medicinal need for developing the protection and treatment against metabolic syndrome especially using safe and beneficial natural compounds.

Hectic research thus continues in this field, with a special interest for alternative solutions, especially those based on products of plant origin, as the plant derived products are considered to be natural and safe, in opposition to the commercial drugs of synthetic origin. Keeping this in mind, in conjunction with the urgent need for the control and treatment of metabolic syndrome and the disease conditions associated with metabolic syndrome, the inventors have conducted extensive research investigation involving several in vitro and in vivo experiments on several plant extracts, fractions and pure compounds and accidentally found that administration of one or more of the components selected from the extracts, fractions, active compounds derived from the herb *Holoptelea integrifolia* in a therapeutically effective amount to the adipocyte cells potently ameliorated the levels of certain biomarker molecules or biological proteins that are altered during metabolic syndrome and disease conditions associated with metabolic syndrome, especially atherosclerosis and diabetes.

The extracts of *Holoptelea integrifolia* leaves were tested for anti-adipogenesis and prolipolytic activity in cell based in vitro assays on 3T3-L1 cells. The methanol extract (LI/PD/083/03) and hydroalcohol extract (60% methanol) (LI/PD/083/02) has shown potent anti-adipogenesis and prolipolytic activities (Table 1 & 2) as described in the inventors previous PCT application # PCT/IN07/000356. The inventors have evaluated the modulation of protein expression of metabolic biomarker molecules in 3T3-L1 adipocytes during metabolic processes by 60% methanol/$H_2O$ extract of *Holoptelea integrifolia* (LI/PD/083/02) using an immunoblot assay. Briefly, the 3T3-L1 cells were differentiated in the presence and absence of LI/PD/083/02 and equal amount of cell lysates proteins were resolved in 7.5% SDS-PAGE; thereafter, the proteins were transferred to nitrocellulose membrane. After blocking the non-specific sites, the membrane was incubated with either anti-PPARγ, or anti-ADRP, or anti-adipo-CD36, or anti-aP2, or anti-β3AR, or anti-perilipin antibody. Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. It was found surprisingly that the adipocyte differentiation markers such as Peroxisome proliferator-activated receptor gamma (PPARγ), CD36, Fatty Acid Binding Protein 4 (aP2/FABP4) and intracellular lipid droplet surface associated protein (perilipin) expression were potently inhibited by LI/PD/083/02 (FIG. 1) in a dose dependent manner.

The macrophage CD36 is considered as a potential biological marker for high risk factor of accelerated atherosclerosis. Inhibition of CD36 protein expression in high glucose induced J774 macrophage cells in presence of hydroalcohol extract (LI/PD/083/02) of *Holoptelea integrifolia* leaves was evaluated using immunoblot assay and compared with the expression obtained for the control group treated with a placebo. As described above, the cell lysate proteins was resolved and transferred to nitrocellulose membrane. After blocking the non-specific sites, the membrane was incubated with CD36 antibody (R&D Systems, Minneapolis, Minn.). Finally, the specific immuno-reactive bands were developed, immunoblot images were recorded and Band intensities were calculated densitometrically and normalized with expression of actin in respective samples. The results are summarized in FIG. 2. The representative immunoblot image indicated that LI/PD/083/02 significantly inhibited the CD36 protein expression in high glucose induced J774 macrophage cells. This unexpected observation provides the argument in favor of anti-atherosclerotic properties of 60% methanol extract of the leaves of *Holoptelea integrifolia*.

The down regulation of several marker proteins in LI/PD/083/02 treated adipocytes suggests that the hydroalcohol extract of *Holoptelea integrifolia* (LI/PD/083/02) exerts multiple beneficial roles in controlling the adipogenic differentiation process; by (1) inhibiting cellular differentiation by down regulating PPARγ, which is a nuclear receptor protein that functions as a transcription factor for regulation of cellular differentiation, development and metabolism. (2) restricting cholesterol ester uptake by inhibiting CD36, which is a class B scavenger receptor involved in lipid uptake, (3) decreasing intracellular adiposity and intracellular lipid transport by reducing FABP4/aP2 level, which acts as a transport protein for long chain fatty acids. Moreover, downregulation of perilipin protein in *Holoptelea integrifolia* (LI/PD/083/02) treated adipocytes strongly indicate the reduction of fat stores in cytoplasm. Perilipin is a protein that coats lipid droplets in adipocytes. It offers protection from the action of hormone-sensitive lipase, which breaks triglycerides into glycerol and free fatty acids for use in metabolism or lipolysis. Therefore it is indicative that hydroalcohol extract of *Holoptelea integrifolia* provides such a state where the stored lipids are more susceptible to enzymatic break down into glycerol and free fatty acids by thinning the perilipin coat around the lipid filled vesicles.

Similarly, the modulation of adiponectin protein by methanol extract (LI/PD/083/03) of the leaves of *Holoptelea integrifolia* in 3T3-L1 adipocytes was evaluated in Western immunoblot assay. The cell culture, treatment protocol and immunoblot assay methodology were as per the standard protocol as described briefly above for metabolic markers. The methanol extract LI/PD/083/03 unexpectedly showed significant upregulation of adiponectin protein expression in 3T3-L1 mature adipocytes in a dose dependent manner as summarized in FIG. 3. Adiponectin is a hormone secreted by adipocytes. It reduces intracellular triglyceride content and up-regulates glucose uptake by potentiating insulin signaling thus it provides protection from both adipogenicity and from developing insulin resistant diabetes or type 2 diabetes. Therefore, our finding indicates that methanol extract LI/PD/083/03 of *Holoptelea integrifolia* provide protection against developing obesity, insulin resistance or Type 2 diabetes, atherosclerosis and attenuates endothelial dysfunction disorders as well. LI/PD/083/03 can also be useful in the treatment and control of metabolic syndrome.

It was quite unexpected to see that a single ingredient derived from *Holoptelea integrifolia* could able to ameliorate the marker proteins related to many disease conditions associated with metabolic syndrome. This unexpected result suggests that *Holoptelea integrifolia* could be a potential therapeutic agent to control, treat and maintain metabolic syndrome, atherosclerosis, diabetes, endothelial dysfunction in animals and humans.

The extracts of *Holoptelea integrifolia* were then combined with other herbal extracts and tested for their efficacy. It was also found surprisingly that a composition comprising LI/PD/083/02 and methanolic extract of the root of *Withania somnifera* (LIPD/003/03) at a ratio of 2:1, herein after referred to as composition-1, significantly alleviated diet induced metabolic syndrome and disease conditions associated with metabolic syndrome. Supplementation of rats having dietically induced metabolic syndrome with composition-1 significantly reduced body weight, abdominal fat, serum cholesterol and triglycerides. The serum adiponectin concentration was significantly enhanced in the treatment group supplemented with composition-1. The Metabolic syndrome was induced in Sprague Dawley Rats by feeding the rats high fat and high cholesterol diet containing roasted bengal gram, sucrose, milk powder, mineral salt mixture, yeast, butter, groundnut oil and cholesterol for 8 weeks. Following 8 weeks induction phase, the animals were treated daily either with 250 mg/kg body weight of composition-1 or 7 mg/kg body weight of sibutramine in 10 mL of 0.5% CMC for further 8 weeks. The control group of animals were received only the vehicle (10 mL of 0.5% CMC) during this period.

Figure 4A:
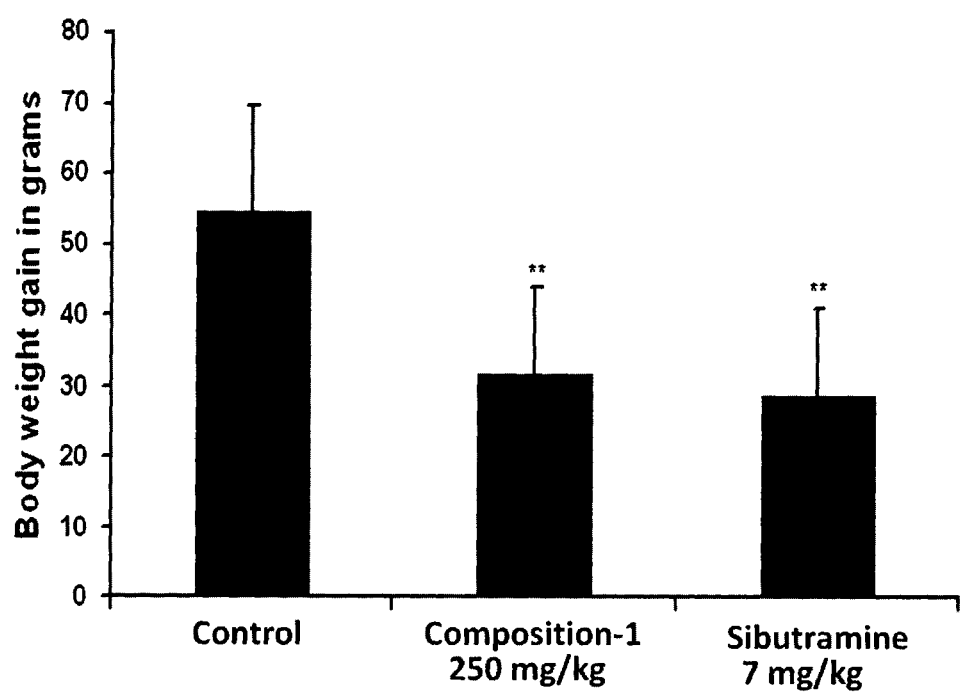
FIG. 4A: Represents body weight gain in grams during treatment with vehicle or various treatments, one group with Composition-1 at 250 mg/kg and the other group with Sibutramine at 7 mg/kg in a rat model of metabolic syndrome. Metabolic syndrome was induced in Sprague Dawley rats by feeding high glucose and fat rich diet for 56 days and then supplemented with either Composition-1 or sibutramine for further 56 days. The control animals were fed only fat rich diet through out the entire span of experiment.
[** indicates statistically significant reduction in weight gain].
Figure 4B:
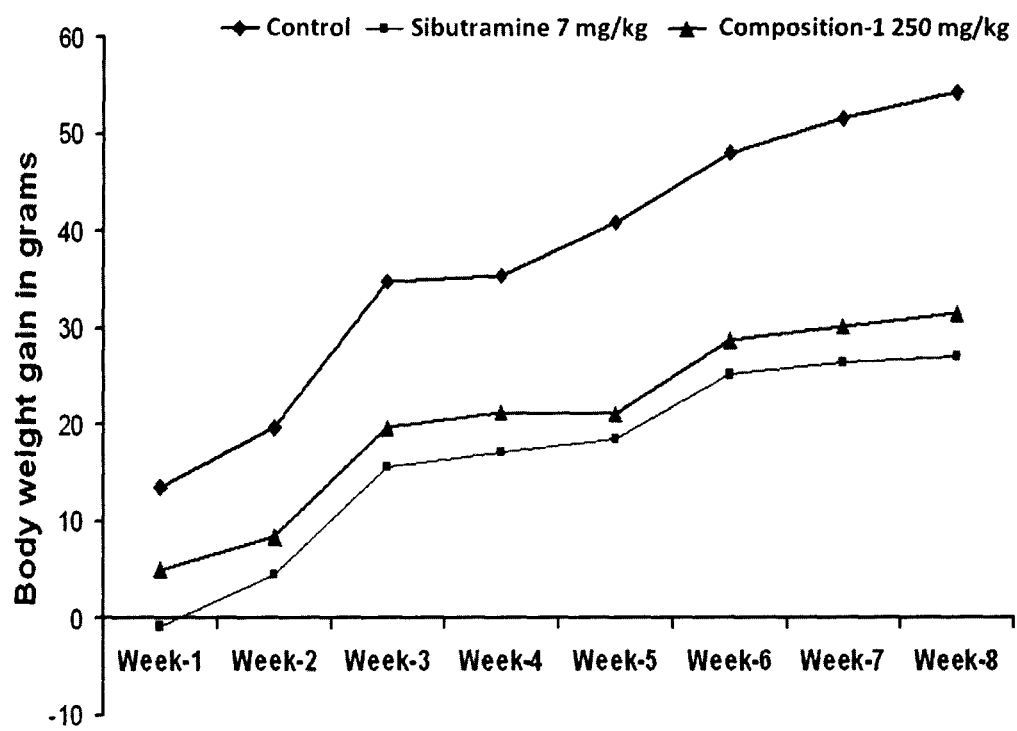
FIG. 4B: Represents comparative body weight gain between control and various treatment groups from week 1 to week 8 of treatment in a rat model of metabolic syndrome.
Figure 5:
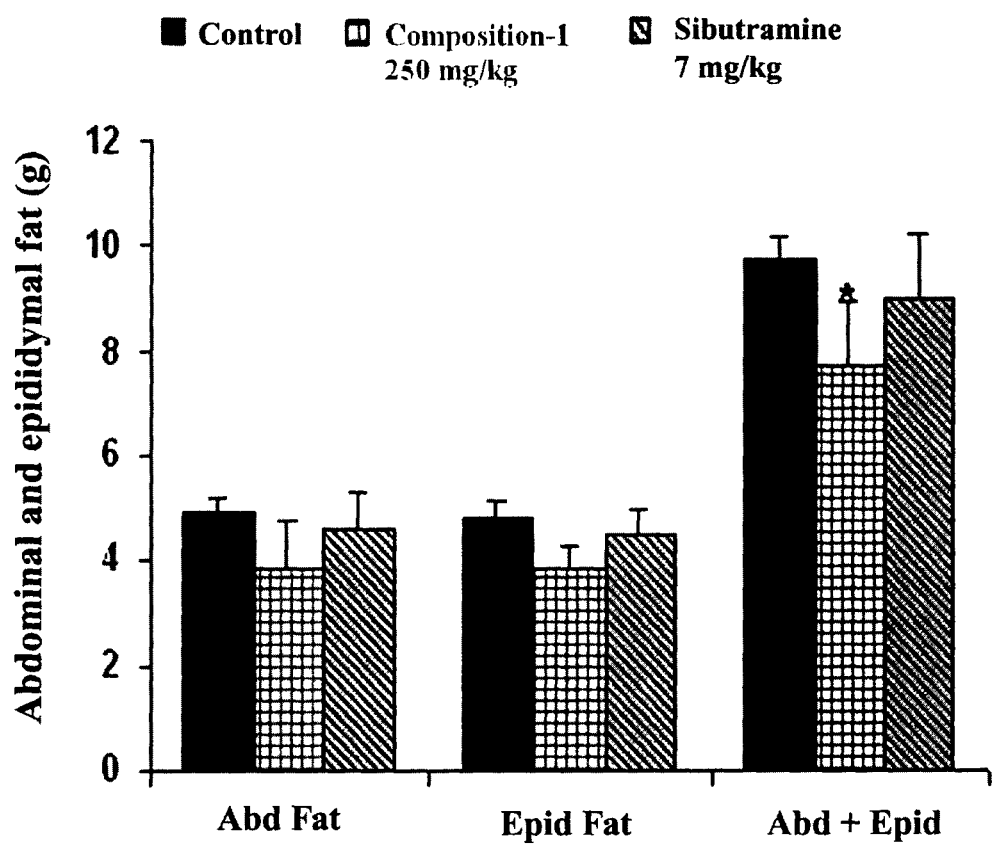
FIG. 5: Represents abdominal, epididymal and abdominal+epididymal fat in grams at the end of 56 days treatment with vehicle or Composition-1 at 250 mg/kg or Sibutramine at 7 mg/kg in a rat model of metabolic syndrome.
[* indicates statistical significance $p<0.05$].
Figure 6A:
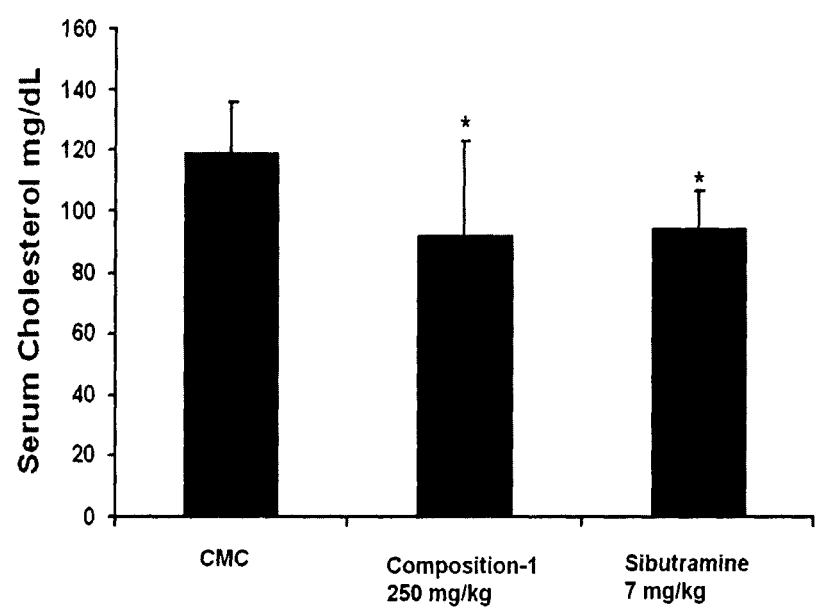
FIG. 6A: Represents serum total cholesterol in mg/dL at the end of 56 days treatment with vehicle or various treatments either with Composition-1 at 250 mg/kg or with Sibutramine at 7 mg/kg in a rat model of metabolic syndrome.
Figure 6B:
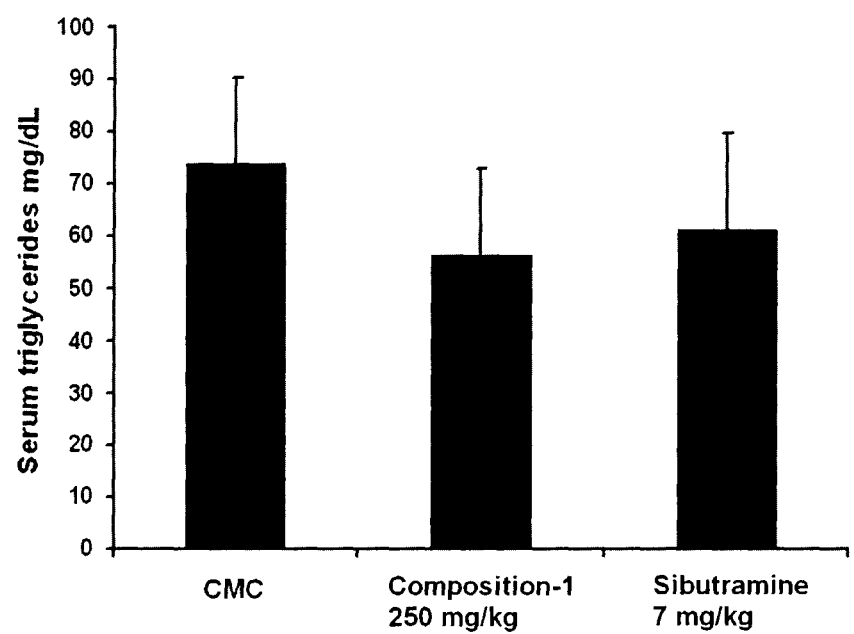
FIG. 6B: Represents serum triglycerides in mg/dL at the end of 56 days treatment with vehicle or Composition-1 at 250 mg/kg or Sibutramine at 7 mg/kg in a rat model of metabolic syndrome.

At the end of the study period it was found very surprisingly that the body weight gain was significantly reduced in the treatment group supplemented with composition-1 compared to the control group supplemented with a placebo as depicted in FIGS. 4A and 4B. By the end of eight week treatment period the total fat (epididymal fat+abdominal fat), serum cholesterol, serum triglycerides were also significantly reduced in the composition-1 supplemented group compared to the placebo treated group as shown in FIGS. 5, 6A, and 6B respectively.

Figure 7:
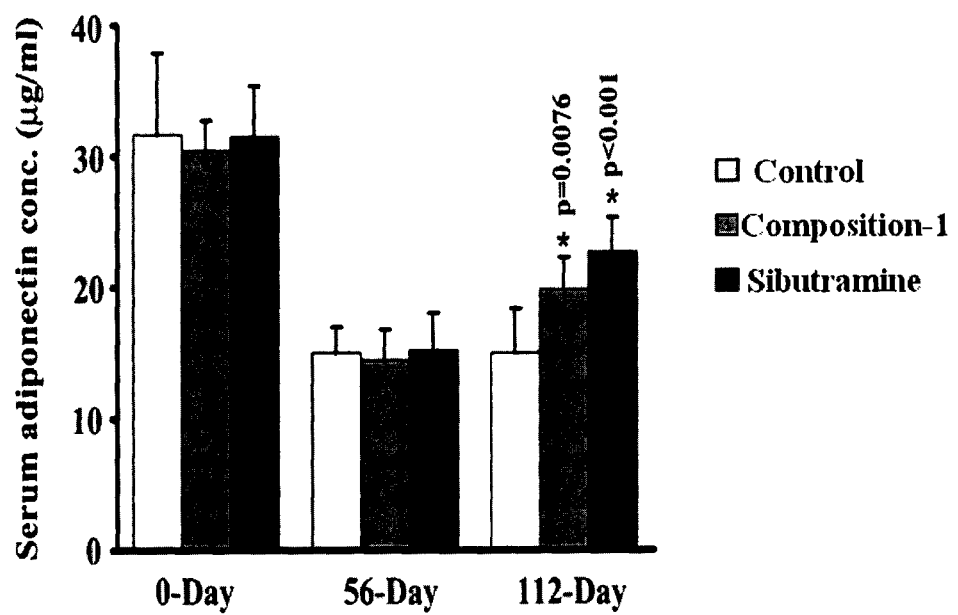
FIG. 7: Illustrates Bar diagram representing improvement in serum adiponectin concentration (μg/ml) in diet induced rat model of metabolic syndrome supplemented with Composition-1 for 56 days, when compared to control and sibutramine supplemented groups. Each bar represents mean±SD (n=8). Serum adiponectin concentrations were measured by Rat Adiponectin ELISA kit (Linco Research, MO, USA). * P values are obtained from one-way Anova, compared with the control group.

In addition the serum adiponectin levels were also significantly modulated in composition-1 treated group compared to the placebo. The plasma adiponectin concentrations are known to inversely related to body weight and insulin levels, insulin resistance and traditional cardiovascular risk factors, such as blood pressure, heart rate, and total and low density lipoprotein (LDL) cholesterol and triglyceride levels, and is positively related to high-density lipoprotein (HDL) cholesterol levels. The serum adiponectin concentrations were evaluated i) on the day of initiation of the study, ii) on the day of initiation of the treatment and iii) on the day of completion of the treatment, using double antibody based sandwich rat adiponectin ELISA kit supplied by Linco Research, USA. The serum adiponectin levels were significantly reduced in all the study groups by the end of 8 weeks metabolic syndrome induction period. However, these levels were significantly enhanced in the treatment group supplemented with composition-1 (FIG. 7).

The foregoing manifested unexpectedly that the hydroalcohol extract of *Holoptelea integrifolia* (LI/PD/083/02) and compositions comprising LI/PD/083/02 are potential agents for the prevention, treatment and control of metabolic syndrome and disease conditions associated with metabolic syndrome. Especially, LI/PD/083/02 and its compositions can be potential agents for the prevention, treatment and control of cardiovascular risk factors, endothelial dysfunction, chronic kidney diseases, diabetes and atherosclerosis. LI/PD/083/02 and its compositions could also be potential agents for the prevention, treatment and control of diabetes and insulin resistance.

Even though a few selected extracts have been used in the present studies, the herb powders, extracts, active fractions and active compounds derived from *Holoptelea integrifolia* can also be used. Preferably an organic solvent extract or aqueous extract or mixed solvent (mixture of organic solvent and water) of *Holoptelea integrifolia* or fraction(s) or pure compound(s) derived from the extract can be used. The medium for obtaining active extract may be selected from either organic solvents or aqueous or mixtures thereof, preferably organic solvent or hydroalcohol. The list of organic solvents include but not limited to hexane, dichloromethane, chloroform, ethyl acetate, acetone, methanol, hydroalcohol, ethanol, propanol, n-butanol, iso-propanol, methyl isobutyl ketone etc., or the mixtures thereof.

Even though methanol extract of *Withania somnifera* has been used to make composition-1, the herb powders, other active extracts, active fractions and active compounds derived from *Withania somnifera* can also be used to prepare composition with *Holoptelea integrifolia* derived agents.

The extract(s), fraction(s) or pure compound(s), hereinafter referred as phytochemical component(s) or agents derived from *Holoptelea integrifolia* can be used directly or as a composition in combination with an excipient or other extracts or phytochemicals or mixtures thereof.

The inventive composition comprises at least one component selected from the powder(s), the extract(s), active fraction(s), active compound(s) and molecules isolated from *Holoptelea integrifolia* and optionally comprising pharmaceutically or dietically acceptable vehicle(s) or carrier(s) for the control and prevention and treatment of metabolic syndrome and disease indications associated with metabolic syndrome.

The invention is unique and the phytochemical components or agents derived from *Holoptelea integrifolia* or their composition(s) are effective in alleviating Metabolic Syndrome alone and/or one or more of disease conditions associated with metabolic syndrome selected from diabetes, insulin resistance/hyperinsulinemia, increased insulin sensitivity, dyslipidemia, hypertriglyceridemia, chylomicronemia and low HDL-cholesterol, lipoprotein aberrations, decreased triglycerides, elevated uric acid levels, fatty liver, polycystic ovarian syndrome, hemochromatosis (iron overload), acanthosis nigricans (dark patches on the skin), impaired glucose tolerance (IGT), including impaired fasting glucose (IFG), and Type 2 diabetes, hypertension, cardiovascular diseases, endothelial dysfunction and atherosclerosis.

The phytochemical component(s) derived from *Holoptelea integrifolia* or its composition(s) are also effective in the amelioration of metabolic marker proteins including but not limited to Peroxisome proliferator-activated receptor γ (PPAR-γ), Adipocyte Differentiation Related Protein (ADRP), Adipocyte CD36, Macrophage CD36, Adipocyte fatty acid binding protein (ap2/FABP), beta 3-Adrenergic Receptor (β3AR), Perilipin and Adiponectin which are related to metabolic syndrome and play a role in the prevention of atherosclerosis and diabetes in mammals or subjects or patients in need thereof.

The inventors have carried out the exhaustive isolation work on the active extract LI/PD/083/02 using different chromatographic techniques and characterized trigonelline, myo-inositol, piperidine-2-carboxylic acid, uracil, adenine, frideline and α-amyrine. An analytical method was developed to characterize and identify the active extract using trigonelline, myo-inositol and piperidine-2-carboxylic acid.

The different aspects of the present invention are described below:

In primary aspect of the invention, one or more of the phytochemical agents or components selected from the extract(s) and active fraction(s) and purified compound(s) of *Holoptelea integrifolia* or their compositions are effective in the prevention, treatment and control of one or more disease conditions selected from Metabolic Syndrome, cardiovascular risk factors, atherosclerosis, endothelial dysfunction, chronic kidney disease and diabetes and other diseases associated with metabolic syndrome.

In another primary aspect of the present invention, one or more of the phytochemical agents or components selected from the extract(s) and active fraction(s) and purified compound(s) of *Holoptelea integrifolia* or their composition(s) are effective in the amelioration of one or more of multiple biomarker molecules that include but not limited to Peroxisome proliferator-activated receptor γ (PPAR-γ), Adipose Differentiation Related Protein (ADRP), Adipocyte CD36, Macrophage CD36, Adipocyte Fatty-acid-Binding Protein (aP2/FABP-4/A-FABP), beta-3 Adrenergic Receptor (β3AR), Perilipin and adiponectin, whose expression is altered during Metabolic Syndrome, atherosclerosis, diabetes, chronic kidney disease and other diseases associated with metabolic syndrome.

Various exemplary embodiments of the invention provide amelioration of the biomarker molecules or biological proteins that are altered in disease conditions associated with or related to Metabolic Syndrome by administering at least one of the component selected from the extract(s), active fraction(s) and/or purified compound(s) of *Holoptelea integrifolia* and their compositions optionally comprising pharmaceutically or dietically acceptable vehicle or carrier for the control and prevention and treatment of metabolic syndrome and disease indications associated with metabolic syndrome.

Various exemplary embodiments of the invention further provide composition(s) for use in a therapeutically effective amounts for alleviating Metabolic Syndrome, increasing the insulin sensitivity, improve glucose tolerance, lower triglyceride levels and balance glucose levels in mammals and a variety of diseases and conditions of Metabolic Syndrome including but not limited to insulin resistance, glucose intolerance, hyperglycemia, dyslipidemia and hypertriglyceridemia and several related diseases including diabetes, lipoprotein aberrations, altered triglyceride, chylomicronemia impaired fasting glucose, decreased HDL Cholesterol, atherosclerosis, endothelial dysfunction and cardiovascular diseases.

Various exemplary embodiments of the present invention further provides a method of control, prevention and treating the mammals having a condition known as Metabolic Syndrome, cardiovascular diseases, atherosclerosis, chronic kidney disease and diabetes comprising administering to a mammal in need thereof an effective amount of a pharmaceutical, nutraceutical, dietary supplement containing at least one of the components selected from the extract(s), active fraction(s) and/or purified compound(s) of *Holoptelea integrifolia* or a composition comprising said phytochemical components, optionally comprising pharmaceutically or dietically acceptable vehicle or carrier or diluents or mixtures thereof.

Various exemplary embodiments of the invention further provide the usage of the said phytochemical component(s) derived from *Holoptelea integrifolia* and their composition(s)

as it is or in comminuted form and/or in unmodified form as granules, powder, precipitate, extract, dried extract and/or exudates, or the active ingredient(s) can be formulated into a solid, semi-solid or liquid dosage form by adding a conventional biologically or pharmaceutically acceptable vehicle(s) or carrier(s) or diluent(s) or additive(s) or salt(s) or several mixtures thereof for the prevention, control and treatment of metabolic syndrome or component(s) associated with metabolic syndrome.

Various exemplary embodiments of the invention further provides that therapeutically effective amount of the said phytochemical component(s) or composition(s) of the present invention can be administered orally, topically, transdermally or internally or parenterally or in the form of a kit to a subject or patient in need thereof.

Specific dosage form includes for example—tablets, soft capsule, hard capsule, pills, granules, powders, emulsions, suspensions, syrups, pellets, inhalers and parenteral agents and the like.

The amount of composition that will be effective in the treatment of a particular disorder or condition will depend on the nature of the disorder of the condition, which can be determined by standard clinical techniques.

Various exemplary embodiments of the present invention further provides that the compositions may further comprise effective amounts of pharmaceutical or nutraceutical or dietically acceptable antioxidant(s), adaptogen(s), anti-inflammatory agents, anti-obese agents, anti-diabetic agents, bio-protectants and/or bio-availability enhancer(s) and trace metals or an excipient(s) or mixtures thereof to form a formulation administered using any of the method described above.

Various exemplary embodiments of the invention further provides, additional dietary supplement agents that can be used for preparing the compositions comprising phytochemical agents derived from *Holoptelea integrifolia* and the extract(s), fraction(s), active compound(s) or mixtures thereof derived from but not limited to *Withania somnifera, Salacia reticulata, Terminalia chebula, Tinospora cordifolia, Citrullus vulgaris, Dolichos biflorus, Sphaeranthus indicus, Garcinia mangostana, Cassia tora, Cassia auriculata, Azadirachta indica, Tephrosia purpurea, Ginkgo biloba, Lagerstroemia speciosa, Ocimum sanctum, Ficus racemosa, Aegle marmelos,* Cinnamon extract, *Albizia amara, Amorphophallus campanulatus, Gendarussa vulgaris, Piper nigrum, Raphanus sativus* and *Rubia cordifolia.*

The examples of the biologically acceptable carriers or diluents employed in the present invention include but are not limited to surfactants, excipients, binders, disintegrators, lubricants, preservatives, stabilizers, buffers, suspensions and drug delivery systems.

Preferred examples of solid carriers include but not limited to glucose, fructose, sucrose, maltose, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

Preferred examples of liquid carriers (diluents)/additives/excipients include but not limited to, distilled water, saline, aqueous glucose solution, alcohol (e.g. ethanol), propylene glycol, polyethylene glycol, tween-60 and tween-80, and oily carriers such as various animal and vegetable oils, white soft paraffin, paraffin and wax.

In another embodiment the invention provides that the product of the present invention is delivered in the form of controlled release tablets, using controlled release polymer-based coatings by the techniques including nanotechnology, micro encapsulation, colloidal carrier systems and other drug delivery systems known in the art.

Another embodiment of the present invention includes, the phytochemical components derived from *Holoptelea integrifolia* and its compositions can be formulated into any food and drink form such as solid food like cereals, baby food, chocolate or nutritional bars, semisolid food like cream or jam, or gel. Contemplation was also done to formulate the product of the invention into a beverage and the like, such as refreshing beverage, coffee, tea, milk-contained beverage, lactic acid bacteria beverage, drop, candy, chewing gum, chocolate, gummy candy, yoghurt, ice cream, pudding, soft adzuki-bean jelly, jelly, cookie and the like. These various preparations or foods and drinks are useful as a healthy food for the treatment and/or prevention or control of Metabolic Syndrome and related diseases like cardiovascular disease, atherosclerosis and diabetes.

Another embodiment provides that the amount of *Holoptelea integrifolia* derived phytochemical components alone or the composition for administration in the form of above mentioned formulations may not be uniform and varies depending on the nature of the formulation and suggested human or animal dosage of the extract or the fractions, but various preferably, within a range from 0.01 to 500 mg/kg weight/day, more preferably within the range from 0.1 to 50 mg/kg body weight per day.

In another embodiment of the invention, the quantity of *Holoptelea integrifolia* derived phytochemical component(s) or its compositions in the above-mentioned various foods and beverages may not be uniform and varies depending on the nature of the formulation and suggested human or animal dosage of the compositions comprising extracts of *Holoptelea integrifolia,* for example, about 0.001 to 90 wt %, more preferably about 0.001 to 50 wt %.

In further embodiment, the quantity of *Holoptelea integrifolia* derived phytochemical component(s) in the composition varies in the range of 0.001% to 99% by weight based on the total weight of the composition.

Another embodiment of the invention provides that the health care food of the present invention comprises the above phytochemical agents or components or their compositions up to 0.001 to 80%, preferably 0.001 to 50% by weight based on the total weight of the food formulation.

In another embodiment, the invention also describes healthy animal feed obtained by mixing the agents comprising the extract(s), fraction(s) or phytochemical constituents of *Holoptelea integrifolia* and its compositions with various components used in the animal feed for the purpose of controlling, preventing or treating Metabolic Syndrome and several associated or related diseases including but not limited to diabetes, insulin sensitivity, lipoprotein aberrations, altered triglyceride, chylomicronemia, impaired glucose tolerance, impaired fasting glucose, insulin resistance, decreased HDL cholesterol, elevated uric acid levels, fatty liver, non-alcoholic fatty liver disease, polycystic ovarian syndrome, hemochromatosis (Iron overload), acanthosis nigricans (dark patches on the skin) atherosclerosis, endothelial dysfunction and cardiovascular diseases.

In another embodiment, the form of the food additive for animal feed is not specifically limited and the extracts or phytochemical components derived from *Holoptelea integrifolia* or its compositions may be added to food products as it is, or as a composition, to various cooked and processed food products. The quantity may be the same as that used in case of human food products. Similarly, the ingredients may also be added during or after preparation of the animal feeds.

In another embodiment, the invention further includes the method of identification or standardization of the extracts, fractions or active compounds or mixtures thereof derived from *Holoptelea integrifolia*, which comprises the steps of:

i) Preparing standard solutions of trigonelline, myo-inositol and piperidine-2-carboxylic acid and sample solutions of alcohol and hydroalcoholic extract of *Holoptelea integrifolia* by dissolving a known amount of each of these compounds separately in a known volume of 50% methanol.

ii) Application of sample and standard compounds to the pre-activated TLC plate as wide bands positioned at an optimum height from the bottom of the plate using an automated TLC applicator or a manual applicator.

iii) Developing the TLC plates in a glass chamber pre-saturated with the mobile phase n-Butyl alcohol:MeOH:Water:Acetic acid [60:20:10:10] and allowing the solvent front to run to an optimum height, preferably at least 8 cm.

iv) Removing the plate from the glass chamber and resting the plate on a horizontal surface and drying the plate free of the solvent.

v) visualizing the TLC plate under UV-light at 254 nm in an HPTLC system to observe trigonelline as a dark brown spot followed by spraying the TLC plate with ninhydrin solution and heating to visualize myo-inositol as a pinkish brown spot and piperidine-2-carboxylic acid as intense violet spot and then scanning the plate UV-light at 500 nm using HPTLC to qualitatively assess myo-inositol and piperidine-2-carboxylic acid.

vi) comparing the $R_f$ values of the TLC spots corresponding to the sample with those of the standards qualitatively and quantitatively to identify and measure the compositions of the sample of hydroalcohol extract or alcohol extract.

The method of identification of the extract is described in example-8.

In the other aspect, uracil, adenine, frideline and α-amyrine may also be found in minor quantities in the extracts and fractions.

The active extracts and fractions derived from *Holoptelea integrifolia* comprises at least one compound selected from trigonelline, myo-inositol, piperidine-2-carboxylic acid, adenine, uracil, frideline and α-amyrine. The concentrations of these compounds are not constant and the concentration of trigonelline varies in the range from 0.01 to 30%, myoinositol varies in the range from 0.01 to 30% and piperidine-2-carboxylic acid ranging from 0.01 to 30%. Likewise the levels of uracil, adenine, frideline and α-amyrine varies in the range from 0.001 to 5%.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Assessment of Inhibition of Lipid Accumulation in Differentiated Adipocytes by *Holoptelea integrifolia* Extracts (LI/PD/083/03 and LI/PD/083/02)

One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX) for 48 h. After this the medium was replaced by DMEM containing 10 µg/ml insulin and incubated for 3 days. Then the differentiating cells were treated with 10 µg/ml of *Holoptelea integrifolia* hydroalcohol (60% methanol) extract (LI/PD/083/02) or methanol extract (LI/PD/083/03) separately and maintained in the medium for another 3-5 days. The cells incubated with 0.1% DMSO were considered as the vehicle control. After the incubation period, cells were washed with phosphate buffered saline (PBS) and fixed with 10% buffered formalin for 1 h at room temperature. One small aliquot of cell suspension was separated for cell counting in hemocytometer chamber. Fixed cells were stained with Oil Red O solution to measure the cellular neutral lipid accumulation. Briefly, cells were washed with PBS, fixed with 10% buffered formalin and stained with Oil Red O solution (0.5 g in 100 ml isopropanol) for 10 min. After removing the staining solution, the dye retained in the cells was eluted into isopropanol and OD measured at 550 nm. The inhibition of fat accumulation in the treated cells was compared with the mock treated differentiated adipocytes. The treated and control cells were also analyzed and compared for inhibition of lipid accumulation visually under microscope and recorded digitally in suitable image capture system. The anti-adipogenic activity shown by *Holoptelea integrifolia* hydroalcohol (LI/PD/083/02) and methanol extracts (LI/PD/083/03) are summarized in Table 1.

TABLE 1

Anti-adipogenic activity of *Holoptelea integrifolia* extracts and compositions

| S. No | Name of the product | % inhibition of lipid accumulation |
|---|---|---|
| 1 | *Holoptelea* methanol ext (LI/PD/083/03) | 45 |
| 2 | *Holoptelea* hydroalcohol ext (LI/PD/083/02) | 46 |

Example 2

Assessment of Pro-Lipolytic Activity of *Holoptelea* Methanol Extract (LI/PD/083/03) and *Holoptelea* Hydroalcohol Extract (LI/PD/083/02) in Differentiated Adipocytes The pro-lipolytic activity was assessed in mature adipocytes as per the procedure of Chemicon International, USA, by measuring free glycerol secreted into the culture medium during the lipolysis process. One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX). The cells were differentiated for 5 days and then the culture medium was removed. The monolayer was washed twice with wash solution (Hank's balanced salt solution), and then 250 µL of incubation solution (Hank's balanced salt solution plus 2% bovine serum albumin) was added to the wells in triplicate in presence or absence of *Holoptelea integrifolia* extracts, and the cells were further incubated for 16 h. To measure lipolysis, 200 μL of free glycerol assay reagent was added to 25 μL of culture supernatants and controls containing glycerol standard. The samples and the controls were incubated for 15 min, and the absorbance was read at 540 nm. A standard curve constructed from the glycerol was used to calculate the concentration of free glycerol in the culture supernatants. The percentage increase in glycerol concentration in the sample solutions, compared to that in the control containing the known concentrations of glycerol, corresponds to the percentage acceleration of lipolysis by LI/PD/083/03 and LI/PD/083/02. The percentage increase in lipolysis accelerated by different extracts of *Holoptelea integrifolia* are summarized in Table 2.

TABLE 2

Pro-lipolytic activity of *Holoptelea integrifolia* extracts and compositions

| S. No | Name of the product | % acceleration of lipolytic activity |
|---|---|---|
| 1 | *Holoptelea* methanol ext (LI/PD/083/03) | 70.2 |
| 2 | *Holoptelea* hydroalcohol ext (LI/PD/083/02) | 65 |

Example 3

Modulation of Adipogenesis and Lipolysis Related Marker Proteins in LI/PD/083/02 Treated 3T3-L1 Adipocytes Mouse pre-adipocyte 3T3-L1 cells are maintained in Dulbecco's Modified Eagles Medium (DMEM) supplemented with 2 mM glutamine, 4.5 g/L glucose and 10% Fetal bovine serum. Equal number of cells was plated in each well of 24-well culture plates. Cells were pre-treated with 10 and 25 μg/mL of LI/PD/083/02 for 2 h and followed by addition of differentiation medium containing 500 nM insulin, 1.0 μM dexamethasone, and 0.5 mM isobutylmethylxanthine (IBMX) for 48 h. Thereafter, cells were further incubated with post differentiation medium (DMEM containing 100 nM insulin) in presence or absence of LI/PD/083/02. Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use. The modulation of adipocyte differentiation markers such as Peroxisome proliferator-activated receptor γ (PPAR-γ), Adipocyte differentiation related protein (ADRP), CD36, adipocyte fatty acid binding protein (aP2); and indicators of lipolysis such as β3-Adrenergic Receptor (β3AR), Perilipin protein expression are evaluated by immunoblot assay.

Inhibition of protein expression of biomarker molecules in adipocytes in presence or absence of LI/PD/083/02 was evaluated in immunoblot assay. Briefly, equal amount of cell lysates proteins were resolved in 7.5% SDS-PAGE; thereafter, the proteins were transferred to nitrocellulose membrane. After blocking the non-specific sites, the membrane was incubated with either anti-PPARγ, or anti-ADRP, or anti-CD36, or anti-aP2, or anti-β3AR, or anti-perilipin antibody, anti-CD36 antibody. Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The data is summarized in FIG. 1.

Example 4

Down-Regulation of CD36 Protein in High Glucose Induced Macrophage Cells, In Vitro Cell Based Model of Diabetes Induced Atherosclerosis by LI/PD/083/02

Inhibition of CD36 production by LI/PD/083/02 was evaluated in glucose induced J774, mouse macrophage cells. Briefly, the cells were cultured in DMEM with 2 mM Glutamine, 100 U/mL penicillin, 100 mg/mL streptomycin and 10% fetal bovine serum (Hyclone, Logan, Utah). Equal number of cells was seeded into 35 mm petri dishes (Corning, USA) one day before the experiment. The culture media was replaced with fresh, glucose free DMEM supplemented with 10% fetal bovine serum. Cells were pre-incubated at 5% $CO_2$ at 37° C. for 2 h with 10 and 25 μg/ml of LI/PD/083/02, and thereafter incubated with 600 mg/dL of glucose for 5 days. The control culture was supplemented with 100 mg/dL glucose. The cells were harvested and lysed with lysis buffer. Cell lysates were clarified at 14,000 g. Protein concentration was measured by Bradford method.

Figure 2:
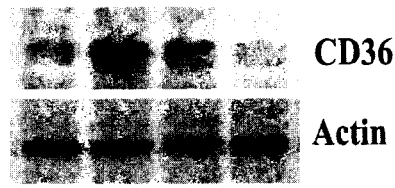
FIG. 2: Illustrates *Holoptelea* extract (LI/PD/083/02) down-regulating high glucose induced CD36 expression in macrophage cells. J774 mouse macrophage cells were exposed to high glucose (600 mg/dL) for 5 days in presence or absence of LI/PD/083/02 at 10 and 25 μg/mL as indicated. Control cultures received low glucose (100 mg/dL). Representative immuno blot assay demonstrates down regulation of CD36 protein and expression of actin protein is considered as the internal control. Bar diagram shows the CD36 expression normalized with actin protein (lower panel).
Figure 2:
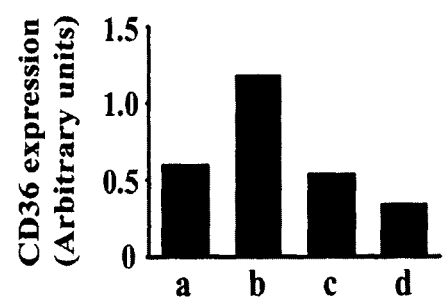

Equal amount of cell lysates proteins were resolved in 7.5% SDS-PAGE; thereafter, the proteins were transferred to nitrocellulose membrane. After blocking the non-specific sites, the membrane was incubated with CD36 antibody (R&D Systems, Minneapolis, Minn.). Finally, the specific immuno-reactive bands were developed with West-pico chemiluminescent substrate (Pierce Biotechnology, IL, USA), and the immunoblot images were recorded in a Kodak Image Station (Kodak, USA). Band intensities were calculated densitometrically and normalized with expression of actin in respective samples. The data as summarized in FIG. 2 showed significant down-regulation of CD36 protein by LI/PD/083/02 in high glucose induced macrophage cells.

Example 5

Figure 3:
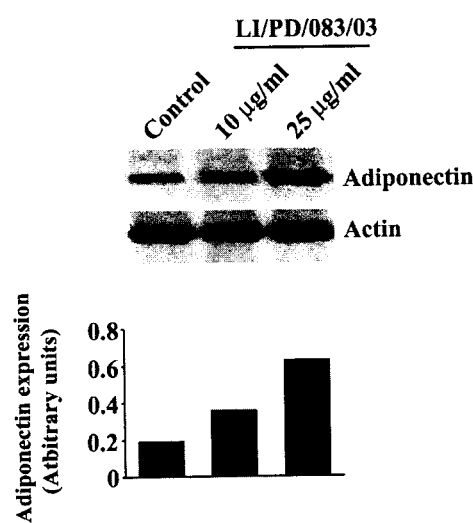
FIG. 3: Representative immunoblot showing over expression of adiponectin protein in LI/PD/083/03 (*Holoptelea integrifolia* leaf methanol extract) treated 3T3-L1 adipocytes in a dose dependent manner. Protein expressions were analyzed densitometrically and normalized with the actin expression. Bar diagram shows normalized protein expressions in arbitrary units. The bars a, b and c represent expression adiponectin in 3T3-L1 adipocytes treated with control, 10 μg/mL and 25 μg/mL of LI/PD/083/02 respectively.

Upregulation of Adiponectin Production by Methanolic Extract of *Holoptelea integrifolia* (LI/PD/083/03) in Mature Adipocytes Modulation of adiponectin protein expression by LI/PD/083/03 in 3T3-L1 adipocytes was evaluated in Western immunoblot assay. The cell culture, treatment protocol and immunoblot assay methodology were the same as described earlier. FIG. 3 represents upregulation of adiponectin protein expression in 3T3-L1 mature adipocytes by LI/PD/083/03 in a dose dependent manner.

Example 6

Preparation of Composition-1, Comprising Hydroalcohol Extract of *Holoptelea integrifolia* (LI/PD/083/02) and Methanol Extract of *Withania somnifera* (LIPD/003/03)

Composition-1 was prepared by mixing 150 g of hydroalcohol extract of *Holoptelea integrifolia* (LI/PD/083/02) and 100 g of methanol extract of *Withania somnifera* (LIPD/003/03). The mixture was pulverized and sieved through 80 mesh.

Example 7

Efficacy of Composition-1 Comprising Hydroalcohol Extract of *Holoptelea integrifolia* (LI/PD/083/02) and Methanol Extract of *Withania somnifera* (LIPD/003/03) in a Diet Induced Metabolic Syndrome Model in SD Rats Animals were acclimatized for 7 days prior to study initiation. A batch of 30 Sprague Dawley Rats was divided randomly into 3 groups, each comprised of 10 animals. Animals were treated orally by daily administration of vehicle-(10 mL of 0.5% CMC/kg) (Group-1) or the test compound Composition-1 (250 mg/kg) (Group-2) or Sibutramine (7 mg/kg) (Group-3). All the animals were treated orally (using oral feeding gavage) with allocated test substance or positive or negative controls daily for 8 weeks. The data is tabulated in Table-3.

TABLE 3

| S. No | Group and treatments | Test article (Dose) | No. of Animals |
|---|---|---|---|
| 1 | Group-1 (Control) | Vehicle 10 mL/kg (0.5% CMC) | 10 |
| 2 | Group-2 | Composition-1 (250 mg/kg) | 10 |
| 3 | Group-3 | Sibutramine (7 mg/kg) | 10 |

Induction Phase:

Metabolic syndrome was induced by feeding the rats high fat, high cholesterol diet containing 32 g of roasted bengal gram, 27 g of Sucrose, 17 g of milk powder, 5 g of mineral salt mixture, 1 g of yeast, 2 g of butter, 11 g of groundnut oil and 5 g of cholesterol per 100 g of the diet for 8 weeks.

Treatment Phase:

Following 8 weeks induction phase, the animals were treated orally with 250 mg/kg body weight of Composition-1 or 7 mg/kg body weight of sibutramine in 10 mL of 0.5% CMC for further 8 weeks. The control group of animals were received only the vehicle (10 mL of 0.5% CMC) during this period. In the treatment phase, all animals were provided with the standard rodent diet till the end of the study. Body weight of individual animal was recorded weekly in the entire duration of the study. Blood sampling were done via sinus orbital plexus under mild anesthesia, before induction, before initiation of treatment and after completion of treatment. Composition-1 showed statistically significant reduction in weight gain when compared to control group, as depicted in FIGS. 4A and 4B.

Fat Tissue Weight:

Abdominal and epididymal fat were weighed separately at the termination of the study for each animal and the results are summarized in FIG. 5. The weight of abdominal and epididymal fat in both the treatment groups were lower in comparison to control group and the total fat was significantly reduced ($p<0.05$) in Composition-1 treated group and the reduction is better than the sibutramine treated group.

Serum Biochemistry:

Various biochemical parameters including lipid profile were tested using biochemistry reagents supplied by Human, Germany, in an automated clinical chemistry analyzer HumaStar300, Make: Human, Germany. Mean values of the biochemical parameters estimated before induction, after induction/before treatment and after treatment were measured and compared. Both Composition-1 and sibutramine showed statistically significant reduction in serum cholesterol levels as shown in FIG. 6A. Serum triglycerides levels were also reduced significantly in the treatment group supplemented with Composition-1 as summarized in FIG. 6B though the difference is not statistically significant.

Serum Adiponectin:

Adiponectin is a protein hormone which is exclusively secreted from adipose tissue into the blood stream. Serum concentrations of adiponectin for the control and treatment group of animals were assessed using double antibody based sandwich rat adiponectin ELISA kit. The assay was performed following the instructions provided by the manufacturer (Linco Research, USA). The serum adiponectin concentrations were evaluated i). on the day of initiation of the study, ii) on the day of initiation of the treatment and iii) on the day of completion of the treatment. The sensitivity of the assay is 0.155 ng/ml. The mean serum adiponectin levels in different treatment groups and in the control group are summarized in FIG. 7.

Example 8

Method of Identification of *Holoptelea integrifolia* Extract

Preparation of Standards and Sample:

Standard solutions of trigonelline, myo-inositol and piperidine-2-carboxylic acid and sample solutions of methanol extract or hydroalcohol extract of *Holoptelea integrifolia* were prepared by dissolving 10 mg each of these components separately in 10 mL of 50% methanol.

Procedure for High Pressure Thin Layer Chromatography [HPTLC]:

Chromatography was performed on pre-activated (at 110° C.) Merck silica gel 60 F254 HPTLC plates (10×10 cm; 0.25 mm layer thickness). Sample and standard compounds were applied to the layer as 8 mm wide bands, positioned at 10 mm from the bottom of the plate using an automated TLC applicator Linomat IV (CAMAG TLC-Scanner 3, Switzerland) syringe at a speed of 12 sec/µl.

The development of TLC layer was performed using a Camag Twin through glass tank which has been pre-saturated with the mobile phase comprising a 60:20:10:10 mixture of n-Butyl alcohol, MeOH, Water and Acetic acid respectively. The solvent front was allowed to run to a height of 8 cm. After removal from the solvent chamber, the chromatographic plates were dried using hot air blower. Prior to spraying the spray reagent, the components visualized by UV scan at 500 nm. The plates were sprayed with Ninhydrin reagent [Freshly prepared mixture containing 100 mg of Ninhydrin in 10 mL of methanol] and the components visualized with naked eye.

Evaluation:

One dark brown spot was observed at $R_f$ about 0.08 under UV at 254 nm in a HPTLC, which was identical in all respects to spot observed for a standard sample of trigonelline, After spraying the Ninhydrin reagent and heating, one pinkish brown spot was observed at $R_f$ about 0.29 and one intense violet spot observed at $R_f$ about 0.27, which were identical in all respects to the spots observed for the standard sample of myo-inositol and piperidine-2-carboxylic acid respectively. The plates were then scanned under UV at 500 nm on Camag, HPTLC system to further confirm the identity and to do the qualitative assessment.

These standard compounds are visualized and quantified in hydroalcohol extract of *Holoptelea integrifolia* as shown in Table-4.

TABLE 4

| S. No | Standard | RF | % of composition | Evaluation |
|---|---|---|---|---|
| 1. | Trigonelline | 0.08 | 0.36 | Visualized as dark brown spot at 254 nm before spraying Ninhydrin |
| 2. | Myo-inositol | 0.28 | 8.47 | Visualized as pinkish brown spot at 500 nm after spraying Ninhydrin |
| 3. | Piperidine-2-carboxylic acid | 0.26 | 2.30 | Visualized as intense violet spot at 500 nm after spraying Ninhydrin |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A solid oral dosage form for treatment of diseases associated with metabolic syndrome, wherein said dosage form comprises a pill, a tablet, a capsule, or a mixture thereof,
   said dosage form comprising a herbal supplement and a pharmaceutically acceptable excipient, diluent, or additive, said herbal supplement consisting of:
   an effective amount of an herbal extract, said herbal extract comprising:
   from 0.01 to 30% trigonelline, based on the amount of said herbal extract;
   from 0.01 to 30% myoinositol, based on the amount of said herbal extract; and
   from 0.01 to 30% piperidine-2-carboxylic acid, based on the amount of said herbal extract;
   wherein said herbal extract is a hydroalcoholic or organic solvent extract of *Holoptelea integrifolia*; and
   an effective amount of a second herbal agent selected from the group consisting of extracts of *Withania somnifera* roots, *Salacia reticulata*, *Terminalia chebula*, *Tinospora cordifolia*, *Citrullus vulgaris*, *Dolichos biflorus*, *Piper nigrum*, *Rubia cordifolia*, *Sphaeranthus indicus*, *Garcinia mangostana*, *Cassia tora*, *Cassia auriculata*, *Azadirachta indica*, *Tephrosia purpurea*, *Ginkgo biloba*, *Lagerstroemia speciosa*, *Ficus racemosa*, *Aegle marmelos*, Cinnamon extract, and mixtures thereof.

2. The solid oral dosage form according to claim 1, wherein said diseases associated with metabolic syndrome are selected from the group consisting of diabetes, endothelial dysfunction and atherosclerosis.

3. The solid oral dosage form according to claim 1, wherein said herbal extract is present in an amount which is effective for modulating the activity of at least one biomolecule selected from the group consisting of Peroxisome proliferator-activated receptor gamma (PPAR-γ), Adipose Differentiation Related Protein (ADRP), CD36, Adipocyte Fatty-acid-Binding Protein (aP2/FABP-4/A-FABP), beta-3 Adrenergic Receptor (β3AR), Perilipin and Adiponectin.

4. The solid oral dosage form according to claim 1, wherein said herbal extract is an extract of *Holoptelea integrifolia* fruits, *Holoptelea integrifolia* leaves, *Holoptelea integrifolia* flowers, *Holoptelea integrifolia* stem, *Holoptelea integrifolia* bark, *Holoptelea integrifolia* root or mixtures thereof.

5. The solid oral dosage form according to claim 1, wherein said herbal extract is an organic solvent extract of *Holoptelea integrifolia*; an extract of *Holoptelea integrifolia* obtained using a mixture of at least one organic solvent and water; or a combination thereof.

6. The solid oral dosage form according to claim 1, wherein said at least one pharmaceutically acceptable excipient, diluent, or additive is selected from the group consisting of:
   saccharides selected from the group consisting of glucose, fructose, sucrose, maltose, yellow dextrin, white dextrin, sorbitol, corn syrup and microcrystalline cellulose; and
   at least one compound selected from the group consisting of calcium stearate, magnesium stearate, stevioside, lactose, citric acid, tartaric acid, malic acid, succinic acid, lactic acid, L-ascorbic acid, dl-alpha-tocopherol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

7. The solid oral dosage form according to claim 1, wherein said extract of *Holoptelea integrifolia* is present in the solid oral dosage form in an amount of between 0.001% and 99% by weight.

8. The solid oral dosage form according to claim 1, wherein said extract of *Holoptelea integrifolia* is present in the solid oral dosage form in an amount of between 0.001% and 80% by weight.

9. The solid oral dosage form according to claim 1, wherein said extract of *Holoptelea integrifolia* is present in the solid oral dosage form in an amount of between 0.001% and 50% by weight.

10. A solid oral dosage form for treatment of diseases associated with metabolic syndrome, wherein said dosage form comprises a pill, a tablet, a capsule, or a mixture thereof,
    said dosage form comprising a herbal supplement and a pharmaceutically acceptable excipient, diluent, or additive, said herbal supplement consisting of:
    an effective amount of an herbal extract in an amount effective for treatment of diseases associated with metabolic syndrome, said herbal extract comprising:
    from 0.01 to 30% of at least one compound selected from the group consisting of trigonelline, myoinositol, and piperidine-2-carboxylic acid, based on the amount of said herbal extract, and
    from 0.001 to 5% of at least one compound selected from the group consisting of uracil, adenine, frideline and α-amyrine, based on the amount of said herbal extract;
    wherein said herbal extract is an aqueous, hydroalcoholic, or organic solvent extract of *Holoptelea integrifolia*; and
    an effective amount of an extract of the root of *Withania somnifera*.

11. The solid oral dosage form according to claim 10, wherein said herbal extract is an organic solvent extract of *Holoptelea integrifolia*; said organic solvent being selected from the group consisting of hexane, dichloromethane, chloroform, ethyl acetate, acetone, methyl isobutyl ketone, or a mixture thereof.

12. The solid oral dosage form according to claim 10, wherein said herbal extract is an extract of *Holoptelea integrifolia* obtained using a solvent selected from the group consisting of methanol, hydroalcohol, ethanol, propanol, n-butanol, and iso-propanol.

13. The solid oral dosage form according to claim 10, wherein said herbal supplement meets at least one of the following conditions:
   a) the herbal extract is a hydroalcoholic or organic solvent extract of *Holoptelea integrifolia*; and
   b) the extract of the root of *Withania somnifera* is a methanol extract of *Withania somnifera* root.

14. A method of alleviating conditions associated with metabolic syndrome in a mammalian subject in need thereof, comprising administering to said subject a therapeutically effective dose of a solid oral dosage form, wherein said dosage form comprises a herbal supplement and a pharmaceutically acceptable excipient, diluent, or additive, said herbal supplement consisting of:
   an effective amount of an herbal extract comprising:
   from 0.01 to 30% trigonelline, based on the amount of said herbal extract;
   from 0.01 to 30% myoinositol, based on the amount of said herbal extract; and
   from 0.01 to 30% piperidine-2-carboxylic acid, based on the amount of said herbal extract;
   wherein said herbal extract is a hydroalcoholic or organic solvent extract of *Holoptelea integrifolia*; and
   an effective amount of a second herbal agent selected from the group consisting of extracts of *Withania somnifera* roots, *Salacia reticulata, Terminalia chebula, Tinospora cordifolia, Citrullus vulgaris, Dolichos biflorus, Piper nigrum, Rubia cordifolia, Sphaeranthus indicus, Garcinia mangostana, Cassia tora, Cassia auriculata, Azadirachta indica, Tephrosia purpurea, Ginkgo biloba, Lagerstroemia speciosa, Ficus racemosa, Aegle marmelos*, Cinnamon extract, and mixtures thereof.

15. The method according to claim 14, wherein the therapeutically effective dose is between 0.001 to 500 mg/kg body weight/day.

16. The method according to claim 14, wherein said solid oral dosage form comprises a tablet, a capsule, a pill, a granule, a powder, a pellet, or a food for humans or animals.

17. A method of alleviating conditions associated with metabolic syndrome in a mammalian subject in need thereof, comprising administering to said subject a therapeutically effective dose of a solid oral dosage form, wherein said dosage form comprises a herbal supplement and a pharmaceutically acceptable excipient, diluent, or additive, said herbal supplement consisting of:
   an effective amount of an herbal extract in an amount effective for treatment of diseases associated with metabolic syndrome, said herbal extract comprising:
   from 0.01 to 30% of at least one compound selected from the group consisting of trigonelline, myoinositol, and piperidine-2-carboxylic acid, based on the amount of said herbal extract, and
   from 0.001 to 5% of at least one compound selected from the group consisting of uracil, adenine, frideline and α-amyrine, based on the amount of said herbal extract;
   wherein said herbal extract is an aqueous, hydroalcoholic, or organic solvent extract of *Holoptelea integrifolia*; and
   an effective amount of an extract of the root of *Withania somnifera*.

18. The method according to claim 17, wherein the therapeutically effective dose is between 0.001 and 500 mg/kg body weight/day.

19. The method according to claim 17, wherein said solid oral dosage form comprises a tablet, a capsule, a pill, a granule, a powder, a pellet, or a food for humans or animals.

* * * * *